United States Patent
Fouere

(10) Patent No.: US 6,254,562 B1
(45) Date of Patent: Jul. 3, 2001

(54) MEATUS PLUG FOR LACHRYMAL CANAL CAPABLE OF BEING SCREWED

(76) Inventor: Alain Fouere, Thalassa, Bat, II, 120 rue du Commandant Rolland, 13008 Marseille (FR)

( * ) Notice: Subject to any disclaimer, the term of this patent is extended or adjusted under 35 U.S.C. 154(b) by 0 days.

(21) Appl. No.: 09/147,090

(22) PCT Filed: Feb. 4, 1997

(86) PCT No.: PCT/FR97/00216

§ 371 Date: Oct. 2, 1998

§ 102(e) Date: Oct. 2, 1998

(87) PCT Pub. No.: WO98/33461

PCT Pub. Date: Aug. 6, 1998

(51) Int. Cl.$^7$ .................................................. A61M 5/00
(52) U.S. Cl. ......................... 604/8; 604/285; 604/294; 604/9; 128/887
(58) Field of Search .................. 604/8–10, 104, 604/285, 294, 28, 49; 128/898, 864, 887; 606/107, 191, 65–73, 108

(56) References Cited

U.S. PATENT DOCUMENTS

| | | | | |
|---|---|---|---|---|
| 3,949,750 | * | 4/1976 | Freeman | 128/260 |
| 4,959,048 | * | 9/1990 | Seder et al. | 604/9 |
| 5,259,396 | * | 11/1993 | Vrespa | 128/898 |
| 5,259,398 | * | 11/1993 | Vrespa | 128/898 |
| 5,283,063 | * | 2/1994 | Freeman | 424/427 |
| 5,354,299 | * | 10/1994 | Coleman | 606/73 |
| 5,437,625 | * | 8/1995 | Kurihashi | 604/8 |
| 5,584,836 | * | 12/1996 | Ballintyn et al. | 606/73 |
| 5,830,171 | * | 11/1998 | Wallace | 604/8 |
| 5,868,749 | * | 2/1999 | Reed | 606/76 |
| 5,976,139 | * | 11/1999 | Bramlet | 606/66 |
| 6,016,806 | * | 1/2000 | Webb | 128/846 |

\* cited by examiner

Primary Examiner—Richard K. Seidel
Assistant Examiner—Jennifer Maynard
(74) Attorney, Agent, or Firm—Greenblum & Bernstein, P.L.C.

(57) ABSTRACT

The invention concerns a meatus plug for lachrymal canal capable of being screwed, consisting of a substantially cylindrical body (1) whose side surface comprises a helical thread similar to that of a screw for placing or removing the meatus plug by screwing or unscrewing with a tool having a polygonal or cruciform blade used as a screwdriver, the plug comprising or not a through conduit for the passage of a predetermined flow of lachrymal fluid. It is designed for controlling the flow of tears running on the surface of the eye towards the nasal cavity through the lachrymal canals or ducts.

17 Claims, 2 Drawing Sheets

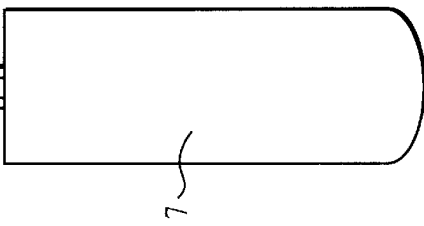
FIG. 9
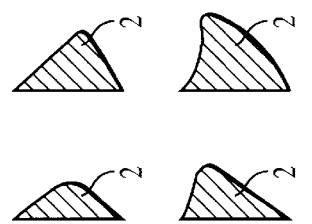
FIG. 5
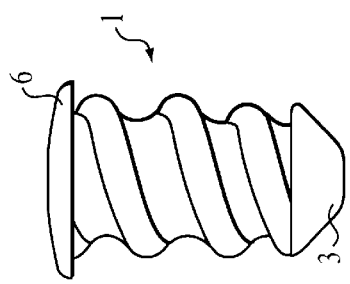
FIG. 8
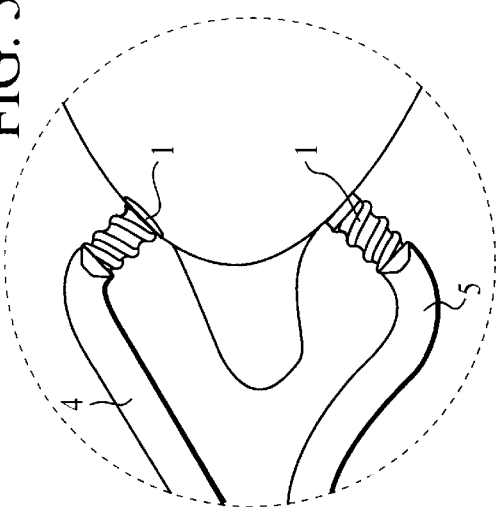
FIG. 7
FIG. 4
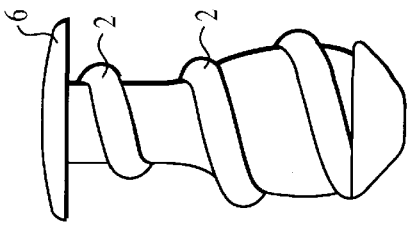
FIG. 6

MEATUS PLUG FOR LACHRYMAL CANAL CAPABLE OF BEING SCREWED

The present invention relates to a meatus plug for lachrymal canal capable of being screwed.

It is adapted to control the flow of tears running over the eye surface towards the nasal cavities through the lachrymal canals or canaliculi.

The normal functioning of the human eye requires that its external surface be constantly covered with a lubricating film constituted by tears, which ensures both rinsing and protection due to the natural anti-infectious antibiotics that they have. They are produced by a series of glands located in the eyelids and in the eye periphery.

The deficiency in maintaining the stability of this film on the eyeball can cause various nuisances, such as tingling, irritations, burning feelings and sight deterioration in case of dryness on the eye surface, or an excess of tears causing red eyes and making the patient wipe his or her face frequently.

Tears are produced continuously, the excess of fluid being drained from the eyeball surface through two upper and lower point openings located near the internal corner of the eye, and communicating with ducts known as canaliculi leading to a lachrymal sac which opens out into the nasal cavity. The point openings, or lachrymal points, have the ability of opening or closing like a sphincter-type muscle, so as to ensure regulating the flow of fluid.

The lack of lachrymal fluid on the eyeball is generally due to a deficiency of the productive glands, which can be caused by age or other factors, particularly, the overly high quantity of tears which can be caused by a blockage of the lachrymal canals. In both cases, the situation can be improved by acting on these canals, either by blocking them completely or partially, or inversely, by keeping them open.

Permanent blockage in particular, possibly by surgery (cauterization, laser) on the lachrymal ducts, can be a method of treatment for the deficiencies related to tears. When the flow of tears into the naso-lachrymal sac is thus prevented, the volume of remaining tears procures a greater wetness.

This method has the drawback of being irreversible, barring a new surgical operation. To overcome this drawback, removable devices have been proposed that can be positioned into a lachrymal canal and removed without a surgical operation. For example, U.S. Pat. No. 5,334,137, filed by the company "EAGLE VISION," describes a device for controlling the lachrymal fluid that blocks the flow of this liquid coming from the eye surface and comprising an end portion in the shape of an inverted truncated cone and a head provided with an enlarged dome. The end portion is arranged to facilitate the positioning of the device through a point opening, and the enlarged dome prevents the complete penetration of the device into the vertical portion of the canaliculus through the point opening.

However, this type of device has risks of accidental migration or expulsion. Furthermore, it requires a particular apparatus for its positioning and extraction, and it does not allow increasing the flow of the lachrymal fluid.

The device according to the present invention has the object of overcoming these drawbacks. Indeed, it allows making meatus plugs that are easily attached and removed without surgical procedure, and without risking involuntary expulsion nor migration towards the innermost part of the lachrymal canals.

It is constituted of a substantially cylindrical body whose lateral surface comprises a helical thread, similar to that of a screw, allowing the positioning or removal of the meatus plug by screwing or unscrewing, with a tool having a polygonal or cruciform blade used as a screwdriver, the plug may or may not comprise an axial through duct allowing the passage of a predetermined flow of lachrymal fluid.

On the attached drawings, which are provided by way of non-limiting examples of embodiments for the object of the invention:

Figure 3:
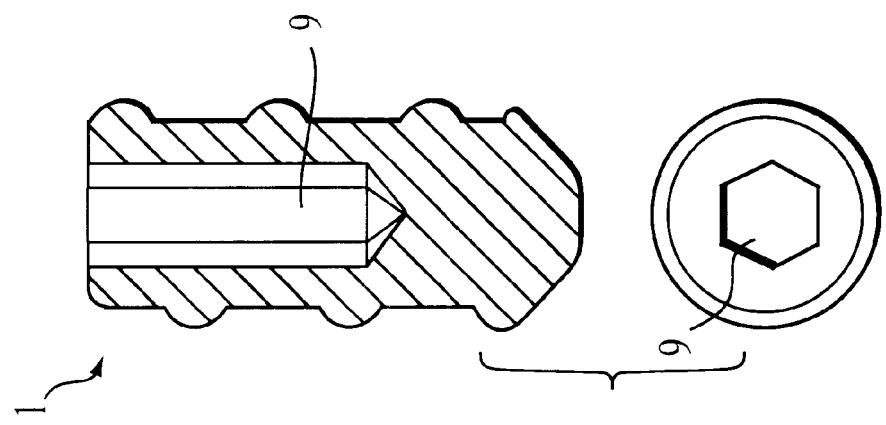
FIG. 3 shows, in the same conditions, an alternative with no collar or through duct.

FIG. 4 schematically shows an eye with the lachrymal canals and the lachrymal sac;

FIG. 5 is an enlargement of the detail A in FIG. 4;

FIGS. 6 and 7 are examples, in a front view, of particular shapes of meatus plugs;

FIG. 8 shows various sections of helical ribbings in a cross-section; and

FIG. 9 shows, on a scale different from the ones used for the plugs, a tool allowing the positioning or removal of a meatus plug.

The device, FIGS. 1–9, is constituted of a body 1 having the general shape of a cylinder whose lateral surface comprises a helical ribbing 2 forming a thread.

The body 1 is provided with a tapered and rounded front end portion 3 which facilitates its introduction into the lachrymal canals 4, 5; the other end portion, or head, possibly comprising a collar 6 adapted to prevent the plug from penetrating too deeply inside a canal. The dimensions of the device are determined to allow it to be inserted into the vertical portion of the lachrymal canals.

The positioning and removal of the meatus plug are carried out by means of a very simple tool, in the shape of a screwdriver, constituted of a handle 7 and a blade 8 having a polygonal, cruciform or similarly shaped section, adapted to penetrate into an axial hole 9 having the same shape provided in the head of the plug.

The hole 9 receiving the blade 8 can be a blind hole (FIG. 3) or be extended by a duct 10 traversing the plug and opening out at the front end portion 3 thereof. In the first case, the device is used as a stopper of the lachrymal canal(s) 4, 5, with the object of preventing the flow of tears towards the lachrymal sac 11. Contrarily, in the second case, the meatus plug is used to increase the flow for eliminating the lachrymal fluid when the lachrymal canals are blocked or when their section is too small.

Figure 2:
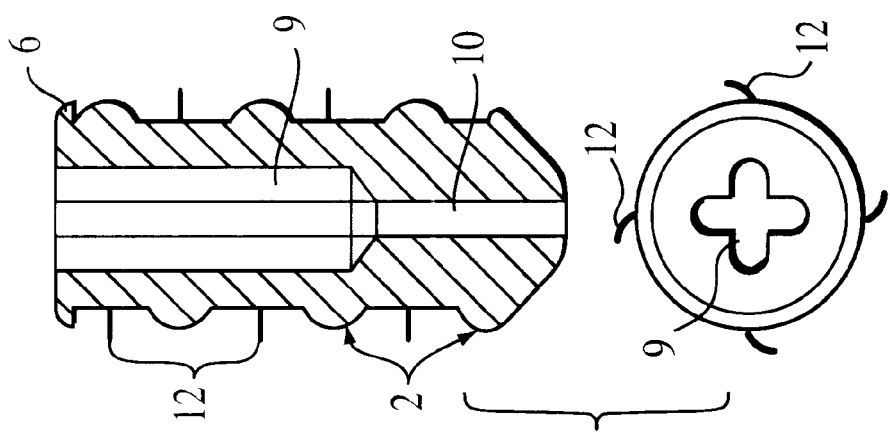
FIG. 2 shows, on a different scale and seen from the top, the same plug in an axial cross-section.
Figure 1:
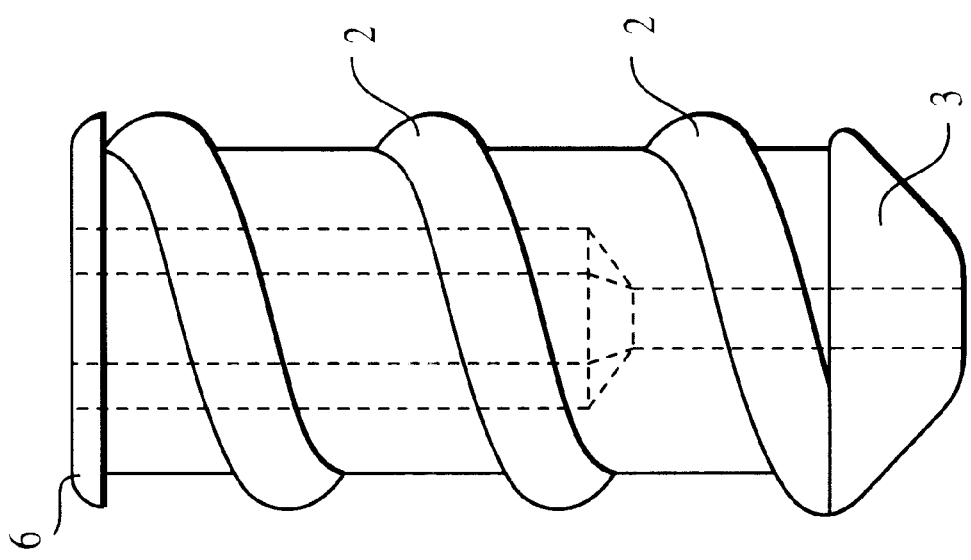
FIG. 1 shows, in a front view, a meatus plug with a collar and a through duct.

The meatus plug according to the invention can be cylindrical (FIGS. 1–3) or have a truncated cone shape (FIG. 7), or yet have one or several bulgings or neckings (FIG. 6). Its lateral surface can be provided with gripping means 12, radially directed outwardly so as to sink into the internal wall of the lachrymal canal, thus preventing any possibilities of displacement of the device, and in particular, a rotation causing a screwing or unscrewing. With this object, the gripping means will advantageously be constituted of curved flexible lugs or filaments (FIG. 2).

The section of the helical thread 2 can also take on various shapes as it appears in FIG. 8. In particular, it can be semi-circular, triangular or trapezoidal.

The body 1 of the plug will be preferably made of a rigid or flexible insoluble synthetic material with a physiological quality, such as silicone, polyethylene or teflon. However, in certain applications, it can be made of an absorbing material, such as hydroxyapatite or cut coral.

The positioning of the various constitutive elements gives the object of the invention a maximum of useful effects which had not yet been achieved by similar devices.

What is claimed is:

1. A meatus plug for screwing into a lachrymal canal and adapted to control the flow of tears running over the eye surface towards the nasal cavities through the lachrymal canals or canaliculi, the meatus plug comprising:

a substantially cylindrical body having dimensions allowing said body to be inserted into the vertical portion of the lachrymal canals, said body having a lateral surface comprising a helical threading, said helical threading adapted to threadedly insert and remove said body into and from the lachrymal canal;

a head at a rear end of said body, said head having a blind axial hole to facilitate the sealing of the lachrymal canal, said blind hole being arranged as one of polygonal or cruciform configuration, said hole penetrating at least halfway through said body, and adapted to be penetrated and driven by a tool having a corresponding mating portion; and a tapered portion at a front end of said body, said tapered portion being tapered and rounded to facilitate the introduction of said body into the lachrymal canals.

2. The meatus plug according to claim 1, wherein said head comprises a collar adapted to prevent said body from penetrating too deeply inside a lachrymal canal.

3. The meatus plug according to claim 1, wherein said lateral surface has gripping portions radially protruding therefrom, said gripping portions adapted to prevent displacement of said body.

4. The meatus plug according to claim 3, wherein said gripping portions each comprise one of a flexible curved lug or a filament, said gripping portions adapted to prevent rotational slippage of said body.

5. The meatus plug according to claim 1, wherein said body is constructed of one of rigid insoluble synthetic material or flexible insoluble synthetic material, said rigid insoluble synthetic material or flexible insoluble synthetic material being one of silicone, polyethylene or Teflon.

6. The meatus plug according to claim 1, wherein said body is constructed of an absorbable material, said absorbable material being one of hydroxyapatite or cut coral.

7. The meatus plug according to claim 1, wherein said body has a frusto-conical shape.

8. The meatus plug according to claim 1, wherein said body has one or more of one of bulgings or neckings.

9. A meatus plug for screwing into a lachrymal canal and adapted to control the flow of tears running over the eye surface towards the nasal cavities through the lachrymal canals or canaliculi, the meatus plug comprising:

a substantially cylindrical body having dimensions allowing said body to be inserted into the vertical portion of the lachrymal canals, said body having a lateral surface comprising a helical threading, said helical threading adapted to threadedly insert and remove said body into and from the lachrymal canal;

a head at a rear end of said body, said head having an axial hole arranged as one of polygonal or cruciform configuration, said hole penetrating at least halfway through said body, and adapted to be penetrated and driven by a tool having a corresponding mating portion; and a tapered portion at a front end of said body, said tapered portion being tapered and rounded to facilitate the introduction of said body into the lachrymal canals; and a cylindrical duct in fluid communication with said axial hole and said front end of said body, said duct penetrating said front end of said body, said duct facilitating lachrymal fluid flow, thereby draining lachrymal fluid when a lachrymal canal is blocked or when a canal section is too small.

10. The meatus plug according to claim 9, wherein said head comprises a collar adapted to prevent said body from penetrating too deeply inside a lachrymal canal.

11. The meatus plug according to claim 9, wherein said lateral surface has gripping portions radially protruding therefrom, said gripping portions adapted to prevent displacement of said body.

12. The meatus plug according to claim 11, wherein said gripping portions each comprise one of a flexible curved lug and a filament, said gripping portions adapted to prevent rotational slippage of said body.

13. The meatus plug according to claim 9, wherein said body is constructed of one of rigid insoluble synthetic material and flexible insoluble synthetic material, said material being one of silicone, polyethylene and Teflon.

14. The meatus plug according to claim 9, wherein said body is constructed of an absorbable material, said absorbable material being one of hydroxyapatite and cut coral.

15. The meatus plug according to claim 9, wherein said body has a frusto-conical shape.

16. The meatus plug according to claim 9, wherein said body has one or more of one of bulgings and neckings.

17. The meatus plug according to claim 9, wherein a circumference of said duct is smaller than a circumference of said axial hole.

* * * * *